US 7,955,306 B2

(12) United States Patent
Wyss et al.

(10) Patent No.: US 7,955,306 B2
(45) Date of Patent: Jun. 7, 2011

(54) ARRANGEMENT FOR INTRODUCING A LIQUID INTO THE BODY OF A PATIENT (75) Inventors: Martin Wyss, Burgdorf (CH); Simon Scheurer, Bern (CH); Reto Aeschlimann, Aefligen (CH); Christian Thalmann, Kehrsiten (CH)

(73) Assignee: Roche Diagnostics International AG, Steinhausen (CH)

( * ) Notice: Subject to any disclaimer, the term of this patent is extended or adjusted under 35 U.S.C. 154(b) by 245 days.

(21) Appl. No.: 12/325,459

(22) Filed: Dec. 1, 2008

(65) Prior Publication Data
US 2009/0171292 A1 Jul. 2, 2009

Related U.S. Application Data (63) Continuation of application No. PCT/CH2007/000075, filed on Feb. 13, 2007.

(30) Foreign Application Priority Data

Jun. 2, 2006 (CH) ........................................ 0888/06

(51) Int. Cl.
*A61M 5/00* (2006.01)

(52) U.S. Cl. .............................. 604/164.12; 604/164.01
(58) Field of Classification Search ............. 604/164.01, 604/164.07, 164.11–164.13, 171, 174–175, 604/177, 179–181, 184, 264, 288.01, 158–162
See application file for complete search history.

(56) References Cited

U.S. PATENT DOCUMENTS

| 5,522,803 | A  | * | 6/1996  | Teissen-Simony ........... 604/177 |
| 5,584,813 | A  | * | 12/1996 | Livingston et al. ........... 604/177 |
| 6,017,328 | A  |   | 1/2000  | Fischell et al. |
| 6,302,866 | B1 | * | 10/2001 | Marggi ........................ 604/174 |
| 7,303,543 | B1 | * | 12/2007 | Maule et al. ............... 604/93.01 |
| 7,704,229 | B2 | * | 4/2010  | Moberg et al. ................ 604/110 |

FOREIGN PATENT DOCUMENTS

| DE | 20 2004 017 862   | 2/2005 |
| DE | 20 2004 017 864   | 2/2005 |
| DE | 20 2004 017860 U1 | 2/2005 |
| DE | 20 2004 017861 U1 | 2/2005 |
| EP | 1 616 594         | 1/2006 |
| WO | WO 02 053220      | 7/2002 |

* cited by examiner

*Primary Examiner* — Nicholas D Lucchesi
*Assistant Examiner* — Melissa A Snyder
(74) *Attorney, Agent, or Firm* — Dinsmore & Shohl LLP

(57) ABSTRACT

An infusion set with a guiding needle, more particularly a laterally displaceable guiding needle.

18 Claims, 12 Drawing Sheets

ARRANGEMENT FOR INTRODUCING A LIQUID INTO THE BODY OF A PATIENT

CROSS REFERENCES TO RELATED APPLICATION(S)

The present invention is a continuation of PCT application No: PCT/CH2007/000075 filed on Feb. 13, 2007 which claims priority to Swiss Patent Application 888/06 filed on Jun. 2, 2006, both of which are incorporated herein in their entirety.

BACKGROUND

The present invention relates to devices for injecting, delivering, infusing, dispensing or administering a substance, and to methods of making and using such devices. More particularly, it relates to infusion sets, an infusion set with a guiding needle, and an infusion set with a laterally displaceable guiding needle.

In patients that regularly require medication, the medication can be administered subcutaneously. For example, for certain groups of patients, e.g. those suffering from pain or patients with type I and type II diabetes, it can be useful to supply the body with a required quantity of medicament in liquid form via a cannula that is arranged in the subcutaneous tissue over quite a long period of time. For this purpose, an arrangement with a cannula made of an elastic material (soft cannula), and designated as an "infusion set" or "port", depending on its design, is secured on the patient's skin in such a way that the cannula passes through the skin and into the subcutaneous tissue. To be able to insert the cannula through the skin into the subcutaneous tissue, it is supported by a guide needle which extends through the inside of the cannula channel and is then removed from the cannula in order to free the cannula channel for the delivery of medicament. Thereafter, the cannula is supplied with the required amount of liquid medicament, in the case of an infusion set by attaching a delivery catheter fed from a medicament-dosing device, or, in the case of a port, by a medicament reservoir that is to be filled at certain intervals by a syringe through a septum.

To avoid infections, the infusion set or the port has to be changed at regular intervals, for example every three days. In outpatient treatment, for example in the case of diabetics, this is often done by the patients themselves. It is therefore important that such infusion sets or ports are inexpensive and can be applied and removed easily and safely, and that their structural design allows operating errors to be ruled out as far as possible from the outset.

The prior art describes various infusion sets in which, after the cannula has been inserted into the tissue, the guide needle is manually removed from the infusion set in the axial direction via a grip part or by a spring-assisted retraction device. However, in such arrangements there is a possibility of the cannula being pulled completely or partially out of the puncture site. In addition, there is also a possibility that the user is injured by the unprotected guide needle.

The prior art also discloses infusion sets in which a flexible guide needle is pulled out of the infusion set via the medicament channel by various retraction devices, the guide needle being deflected through more than 90° by the boundary walls of the medicament channel and being further deformed in the retraction device. The retraction device, with the guide needle located in it, is then removed from the infusion set. Since the guide needle is received in the retraction device, these infusion sets do not pose any risk of injury to the operator. However, the deflection of the guide needle in the medicament channel poses a possibility of material being abraded from the boundary walls of the medicament channel, which may then be carried with the medicament into the subcutaneous tissue of the patient. Moreover, the production of practical designs according to this concept is difficult and expensive.

Therefore, there is a need in the medical device industry to make an infusion set wherein the guide needle can be safely removed from the cannula.

SUMMARY

It is against the above background that the present invention provides unobvious advantages and advancements over the prior art.

One of the objects of embodiments of the present invention is provide a device such as an infusion set comprising a cannula for introducing a liquid such as a liquid medication or a diagnostic substance into the body of a patient or for removing a liquid from the body of a patient, where a guide needle can be safely removed from the cannula after the infusion set is inserted into the skin of a user. In one embodiment, the infusion set delivers the liquid subcutaneously to the body of the user.

In one embodiment, the present invention comprises an infusion set with a guiding needle, more particularly a laterally displaceable guiding needle.

In one embodiment, the present invention comprises an infusion set for introducing a substance into the body of a patient, the infusion set comprising a cannula housing carrying a hollow cannula extending from the housing and a channel, wherein the channel provides a flowpath for a substance to flow generally through the housing to an inlet opening of the cannula, a guide needle for supporting the cannula as the cannula is inserted into the body of the patient, the guide needle being movable in the channel, wherein the guide needle is in the inlet opening after the cannula is inserted into the body of the patient, a deflection element for deflecting the guide needle during the movement of the guide needle in the channel, and a retraction device for retracting the guide needle from the inlet opening. In some embodiments, the guide needle is deflected as it is being moved in the channel, e.g. retracted, and, in some embodiments, the deflection is generally orthogonal, i.e., approximately ninety degrees.

In one embodiment, the infusion set comprises a cannula housing that carries a flexible cannula (soft cannula). The cannula protrudes from an outer face of the cannula housing and is supported by a guide needle, which is made of metal or plastic and which extends through the cannula channel and emerges with a tip from the outlet end of the cannula directed away from the cannula housing. The cannula housing has a channel through which, after removal of the guide needle from the cannula channel, a liquid, e.g. a liquid medicament or a diagnostic substance, can be guided to the inlet opening of the cannula and from there to an outlet opening at the outlet end of the cannula, or through which a liquid, e.g. a body fluid such as blood, can be withdrawn from the cannula. At a location directly opposite the inlet opening of the cannula and in a continuation of the longitudinal axis of the cannula, the boundary walls of the channel have a sealing element, such as a septum, through which the guide needle emerges from the cannula housing.

In some embodiments, the infusion set further comprises a deflection element for deflecting the guide needle. The deflection element is arranged opposite the site where the guide needle emerges from the aforementioned sealing element of the cannula housing. The deflection element forms a guide in which the guide needle is guided axially and is deflected. The guide needle, between the outlet end of the cannula and its entry into the deflection element, has a rectilinear course. The deflection of the guiding needle takes place in the area of entry of the deflection element. In this way, it is possible to ensure that, despite the deflection in the deflection element, no bending movements can be introduced into the section of the guide needle arranged between cannula and deflection element. In addition, in some embodiments, the arrangement according to the present invention comprises a retraction device for the guide needle, by which the guide needle, upon deflection in the deflection element, can be pulled back (or rearwardly) until it emerges from the cannula channel and frees, opens or clears the inlet opening of the cannula.

In yet another embodiment of the present invention, the cannula housing, the deflection element and the retraction device form an inseparable unit, within which the guide needle remains protected and can not be accessed by an operator after it has been pulled back.

In yet another embodiment, the retraction device is designed in such a way that the guide needle can be pulled back with the latter into a retraction end position in which the guide needle is pulled completely out of the sealing element and the tip of the guide needle is arranged inside the deflection element or the retraction device. At the same time, the cannula housing, the deflection element and the retraction device are connected to one another in such a way that, when the guide needle is in a position other than the intended retraction end position, they from an inseparable unit. Once the guide needle has been pulled back by the retraction device and is situated in the retraction end position, it is possible for at least the retraction device, and if appropriate also the deflection element, to be removed from the cannula housing. After removal of the retraction device, and if appropriate also of the deflection element, from the cannula housing, the tip of the guide needle is arranged, in a manner protected against access by an operator, inside the retraction device, or, if the retraction device and the deflection element form a contiguous, inseparable unit, it is arranged inside the guide section of the deflection element. In such embodiments, and in other embodiments, only the cannula housing is needed for the introduction of liquid medicaments to the patient's body, as a result of which the wearing comfort can be improved.

In yet another embodiment, the retraction device comprises two structural parts which can be moved relative to each other along guides. The first structural part is fixed relative to the cannula housing, while the second structural part is movable relative to the cannula housing and is coupled to the guide needle in such a way that, upon movement of the two structural elements relative to each other, the guide needle is pulled back by the movement of the second structural part.

If the two structural parts are designed as structural elements that can be pushed together in a translational movement, this permits structurally simple and inexpensive solutions.

In one embodiment, the direction of pushing together of the two structural parts lies transverse to the direction of the longitudinal extent of the cannula and is oriented perpendicular to the latter and/or oriented in such a way that, when the arrangement is applied correctly to the body of a person, it extends substantially parallel to the surface of the skin in the area of the application site. This orientation prevents a force acting on the cannula housing in the axial direction of the cannula which could lead to the applied cannula being pulled back out of the tissue when the guide needle is pulled back.

In yet another embodiment wherein the retraction devices has two structural parts, one of the two structural parts is provided with a grip surface or surfaces, which are spaced apart from each other in a direction transverse to the direction of pushing together of the structural parts and support the respective finger pads of the index finger and middle finger of a user. At the same time, the other of the two structural parts has a grip surface which lies opposite these grip surfaces approximately centrally in the direction of pushing together and supports the pad of the user's thumb, in such a way that the two structural parts can be pushed together by a finger movement similar to that used when actuating a syringe. In this way, relatively strong actuating forces for pulling the guide needle back can be applied in an easily controllable manner.

In yet another embodiment, if the two structural parts are designed as structural elements that can be rotated relative to each other, then it is possible to achieve relatively strong retraction forces and relatively long retraction paths.

In some embodiments, the axis of rotation of the two structural parts extends parallel to the direction of the longitudinal extent of the cannula and/or is oriented in such a way that, when the arrangement is applied correctly to the body of a person, it extends substantially perpendicular to the surface of the skin in the area of the application site, since this prevents a force acting on the cannula housing in the axial direction of the cannula as the guide needle is being pulled back.

In the embodiments of the arrangement according to the present invention in which the retraction device comprises two structural parts that can be moved relative to each other along guides, and that are either pushed together or rotated relative to each other to effect the retraction movement of the guide needle, these two structural parts are designed in such a way that, when pushed together or rotated relative to each other, they lock together, in an end position of their movement in which the guide needle is retracted to the maximum extent, in such a way that the retraction movement is irreversible. In this way, incorrect handling after the guide needle has been retracted can be avoided.

In yet another embodiment, the retraction device is designed in such a way that the guide needle can be pulled back with the latter into a retraction end position in which the guide needle is pulled completely out of the sealing element and the tip of the guide needle is arranged inside the guide of the deflection element or inside the retraction device. The cannula housing, the deflection element and the retraction device are connected to one another in such a way that, when the guide needle is arranged in a position other than the intended retraction end position, they form an inseparable unit and, when the guide needle is arranged in the retraction end position, it is possible for at least the retraction device, and if appropriate also the deflection element, to be removed from the cannula housing. After removal of the retraction device, and if appropriate also of the deflection element, from the cannula housing, the tip of the guide needle is arranged, in a manner protected against access by an operator, inside the retraction device or inside the guide of the deflection element.

In yet another embodiment, the retraction device comprises two structural parts which can be moved relative to each other along guides, of which the first structural part is fixed relative to the cannula housing, while the second structural part is movable relative to the cannula housing and is coupled to the guide needle in such a way that, when the two structural elements are moved relative to each other, the guide needle is pulled back by the movement of the second structural part. The first structural part is secured removably on the cannula housing via a securing mechanism which is locked by the second structural part, and which is freed only after the two structural parts have moved relative to each other into an end position of their movement in which the guide needle is arranged in the retraction end position.

In some embodiments, if the cannula housing has a connection port for a line for delivering a liquid into the channel or for removing a liquid from the channel, which connection port is accessible only after the first structural part has been removed.

In yet another embodiment, the outer face of the cannula housing from which the cannula extends is substantially flat. In some preferred embodiments, the cannula extends substantially perpendicular from this outer face. Such embodiments are suitable as an infusion set for introducing liquid medicaments into the subcutaneous tissue of the abdominal wall of a patient. However, embodiments are also provided in which the cannula does not protrude perpendicularly from the outer face, e.g. at an angle of 30°.

In yet another embodiment, the outer face of the cannula housing from which the cannula extends carries an adhesive layer, e.g. formed by a plaster or suitable adhesive, with which the cannula housing can be affixed by adhesion to the skin of the patient as the cannula is inserted.

In yet another embodiment, the guide needle is deflected through 90° in the guide section of the deflection element, such that the end of the guide needle coupled to the retraction device extends substantially perpendicular to the longitudinal axis of the cannula. In embodiments wherein the retraction devices has two structural parts that can be pushed together in order to effect the retraction movement, this affords the advantage that the direction of pushing together of the two structural parts is in practice oriented perpendicular to the direction of the longitudinal extent of the cannula, such that, when the retraction device is actuated, this prevents a force acting on the cannula housing in the axial direction of the cannula, which could lead to the applied cannula being pulled back out of the tissue. However, in some embodiments, the guide needle is deflected by more than or less than 90°, e.g. by 30°.

These and other features and advantages of the present invention will be more fully understood from the following detailed description of embodiments of the invention taken together with the accompanying claims. It is noted that the scope of the claims is definitely by the recitations therein and not by any discussion of features and advantages set forth herein.

Those skilled in the art will appreciate that elements in the figures are illustrated for simplicity and clarity and have not necessarily been drawn to scale. For example, the dimensions of some of the elements in the figures may be exaggerated relative to other elements to help improve understanding of embodiment(s) of the present invention.

DETAILED DESCRIPTION

This description of embodiments of the present invention is exemplary in nature and is in no way intended to limit the invention or its application or uses.

With regard to fastening, mounting, attaching or connecting components of the present invention, unless specifically described as otherwise, conventional mechanical fasteners and methods may be used. Appropriate fastening or attachment methods include adhesives, welding and other suitable methods or substances. Generally, unless otherwise indicated, the materials for making the invention and/or its components may be selected from appropriate materials such as metal, metallic alloys, ceramics, plastics, etc.

Figure 1:
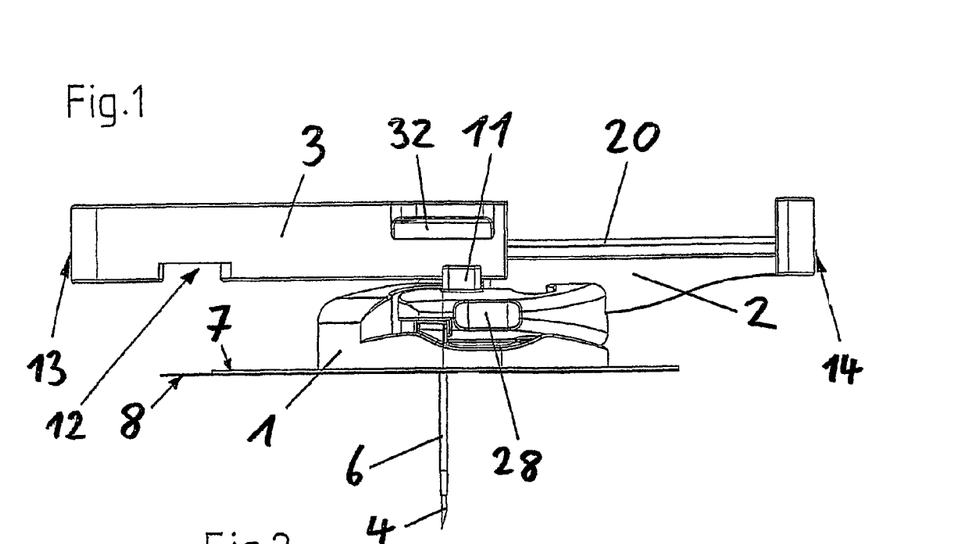
FIG. 1 is a side view of an embodiment of an arrangement according to the present invention before application.
Figure 2:
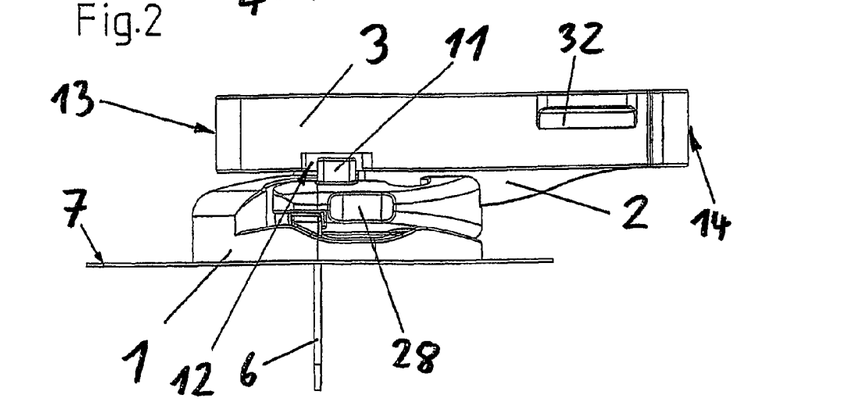
FIG. 2 is a side view of the arrangement of FIG. 1 after application.
Figure 3:
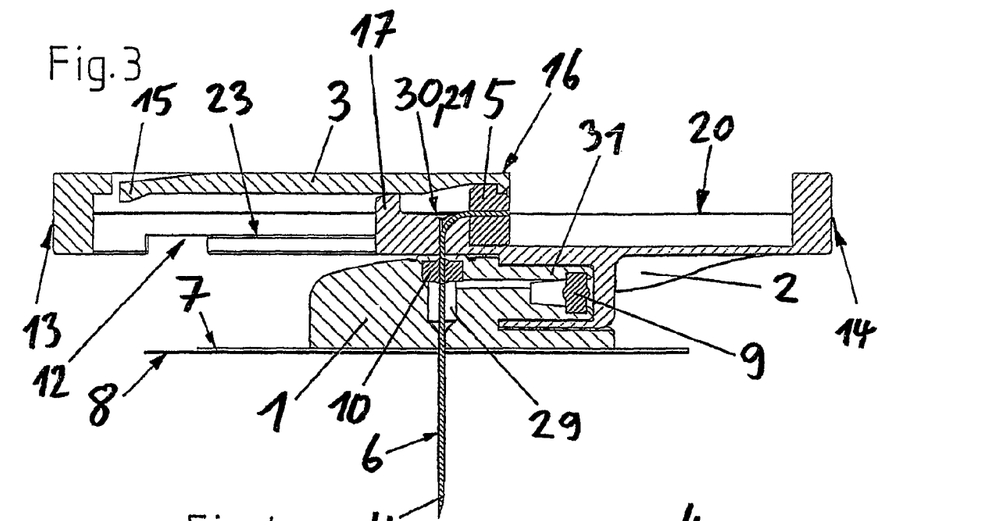
FIG. 3 is a longitudinal section through the arrangement shown in FIG. 1.
Figure 4:
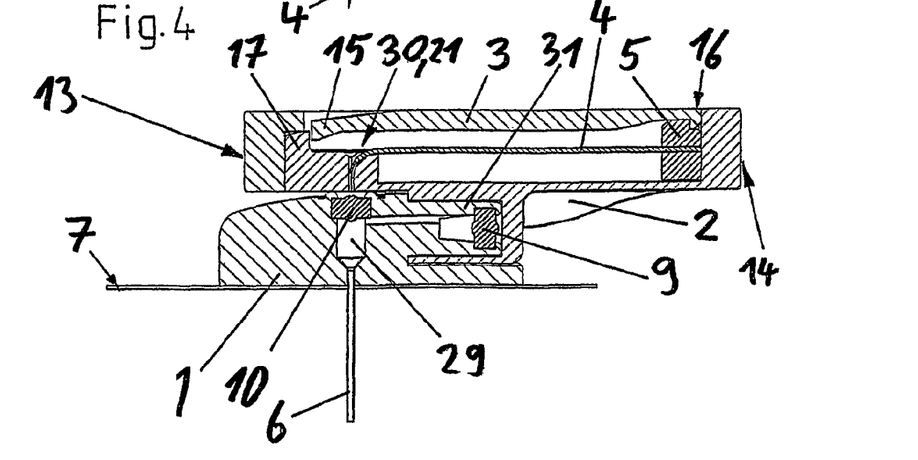
FIG. 4 is a longitudinal section through the arrangement shown in FIG. 2.
Figure 5:
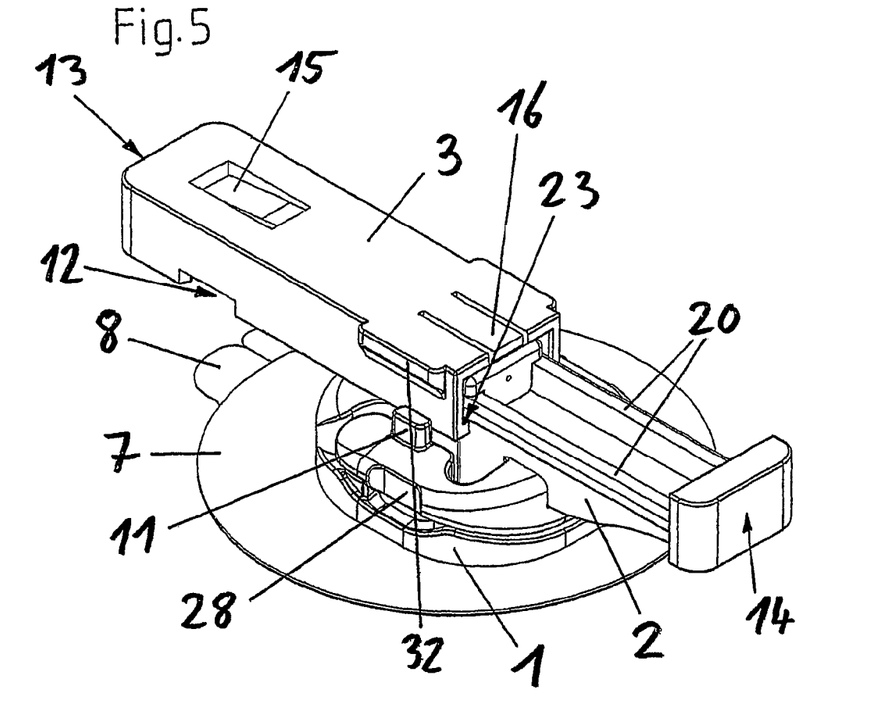
FIG. 5 is a perspective plan view of the embodiment of FIG. 1.
Figure 6:
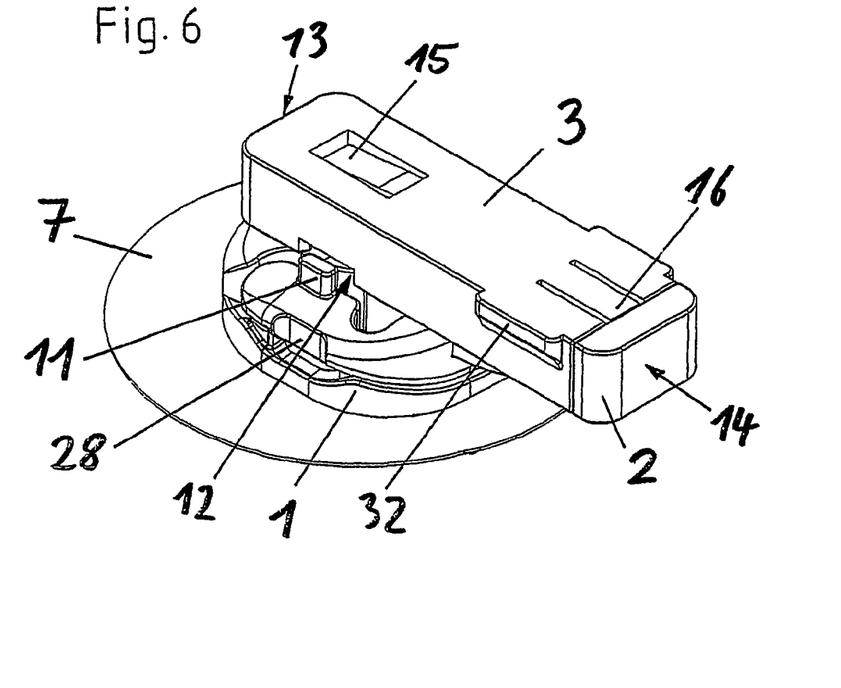
FIG. 6 is a perspective plan view of the arrangement shown in FIG. 2.

One embodiment of an infusion set in accordance with the present invention is shown in side view in FIGS. 1 and 2, in longitudinal section in FIGS. 3 and 4, and in a perspective plan view in FIGS. 5 and 6, in the first instance in an unused original state (FIGS. 1, 3 and 5) and in the second instance in a state after application to the body of a patient (FIGS. 2, 4 and 6).

As can be seen from these figures, the infusion set comprises a cannula housing 1 which, on an underside, carries a cannula 6 made of flexible material and extending perpendicularly from the cannula housing 1. The underside of the cannula housing 1 is formed by a plaster 7 whose adhesive surface in the original state is covered by a protective paper 8. As shown in FIG. 1, in the original state, the cannula 6 has a guide needle 4 extending through its cannula channel, and, to facilitate its penetration into the tissue of a patient, the guide needle 4 forms a tip at the free end (outlet end) of the cannula 6 and supports the flexible cannula 6 during insertion into the tissue. In its interior, the cannula housing 1 forms a channel 29 which extends between the cannula 6 and a first septum 9 forming part of a side wall of the cannula housing 1, such that a liquid medicament can be conveyed from the septum 9 to the inlet opening of the cannula 6. Directly opposite the inlet opening of the cannula 6, and in a rectilinear continuation of the cannula channel, the channel 29 is delimited by a second septum 10, which forms part of the upper face of the cannula housing 1 and through which, in the original state, the guide needle 4 emerges from the upper face of the cannula housing 1.

Arranged on the cannula housing 1 there is a retraction device (in some embodiments comprising elements 2, 3, 5) for pulling the guide needle 4 out of the cannula 6 and out of the second septum 10 after the infusion set has been applied. The retraction device is composed of a fixed housing part 2, a movable housing part 3, and a needle carrier 5 connected to the guide needle 4. The fixed housing part 2 is connected releasably to the cannula housing 1 via snap-fit arms 28, and the movable housing part 3 is mounted on the fixed housing part 2 such that they can be pushed together by sliding via guide rails 20, 23. Opposite the site where, in the original state, the guide needle 4 emerges from the second septum 10 of the cannula housing 1, that end of the fixed housing part 2 directed toward the movable housing part 3 forms a deflection element 30 with a guide 21, in which the guide needle 4, seen in the direction toward the needle carrier 5, is guided axially displaceably in a continuation of the course of the cannula channel and is then deflected through 90°.

To apply the infusion set to the body of a patient, the plaster-protecting paper 8 provided on the infusion set in the original state (FIGS. 1, 3 and 5) is pulled off from the adhesive surface of the plaster 7, and the infusion set is firmly pressed onto the patient's skin via the underside of the cannula housing 1 carrying the plaster 7, in which process the cannula 4 is inserted through the skin into the subcutaneous tissue of the patient, and the cannula housing 1 is secured on the skin by the plaster 7. During insertion, the flexible cannula 6 is supported by the guide needle 4, which also forms the actual insertion tip. The application can in principle be carried out by hand or by using an application aid to which the infusion set can be secured by fastening shoulders 32 formed for this purpose on the movable housing part 3.

After the infusion set has been applied to the skin, the fixed housing part 2 and the movable housing part 3 of the retraction device are pushed together by pressing with two fingers on their end faces 13, 14, in which process the guide needle 4, carrying the needle holder 5 with it, is pulled back by the movable housing part 3 through the deflection element 30 of the fixed housing part 2 until it is completely removed from the cannula housing 1 and the contaminated tip of the guide needle 4 is arranged in a protected state in the guide 21 of the deflection element 30. This situation is shown in FIG. 4.

Figure 10:
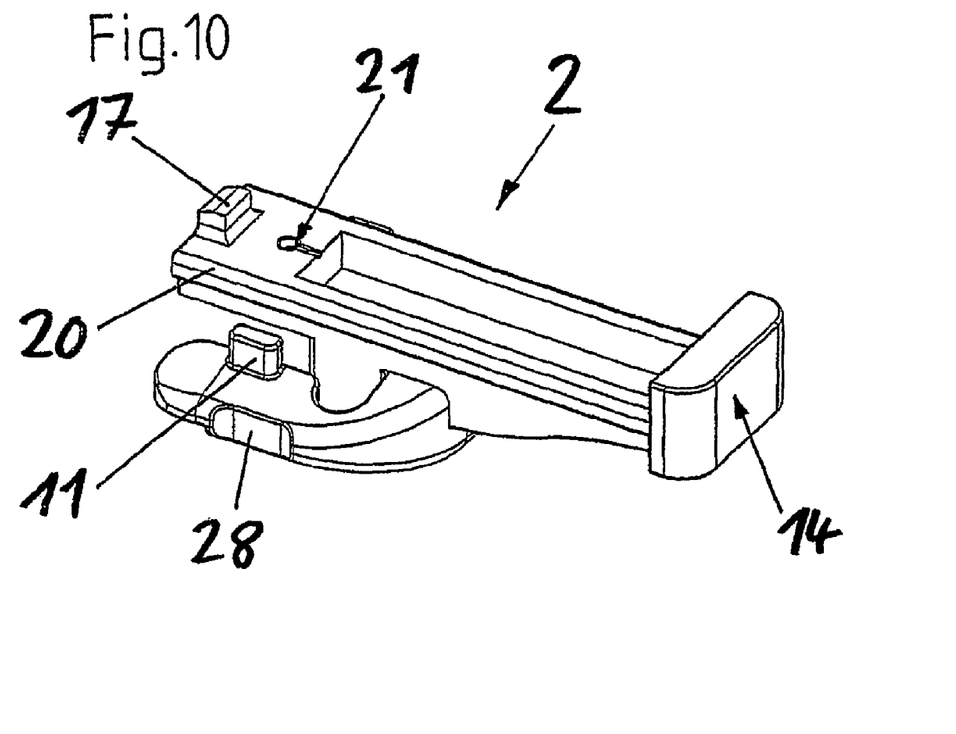
FIG. 10 is a perspective plan view of a fixed part of the retraction device of the arrangement from FIG. 1.
Figure 11:
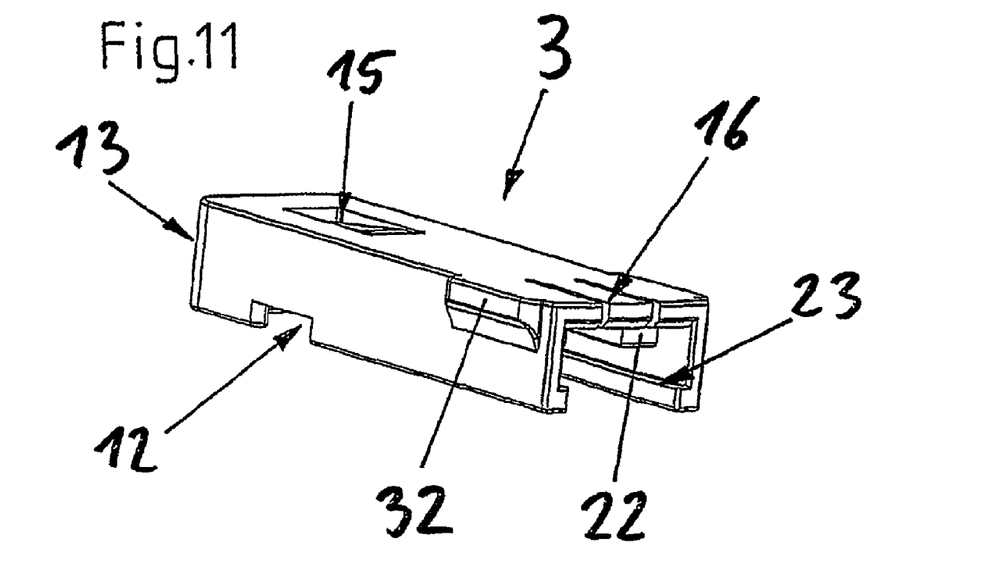
FIG. 11 is a perspective plan view of a movable part of the retraction device of the arrangement from FIG. 1.

As can be seen from FIGS. 10 and 11, which each show a perspective view of the fixed housing part 2 (FIG. 10) and of the movable housing part 3 (FIG. 11), the needle carrier 5 is carried along by a carrier shoulder 22 on the movable housing part 3. After the two housing parts 2, 3 have been completely pushed together, and the guide needle 4 is therefore located in its retraction end position, the catch 15 formed by the movable housing part 3 engages in a locking action with a locking projection 17 formed on the fixed housing part 2, such that the process of pushing together is irreversible. Embodiments are also provided in which an irreversible locking additionally occurs at intermediate positions too, such that, even with the housing parts 2, 3 only partially pushed together, it is no longer possible for the guide needle 4 to slide back into the cannula 6.

After the guide needle 4 has been pulled back completely, the retraction device can be separated from the cannula housing 1 by the snap-fit arms 28 being moved inwardly, with safety cams 11 provided on them moving into cutouts 12 on the movable housing part 3, as a result of which the connection between the cannula housing 1 and the fixed housing part 2 is canceled. In other positions of the two housing parts 2, 3 relative to each other, the safety cams 11, by engaging on the side walls of the movable housing part 3, prevent the snap-fit arms 28 from moving inwardly, such that a separation of cannula housing 1 and retraction device is possible only when the guide needle 4 has been pulled back completely.

Figure 7:
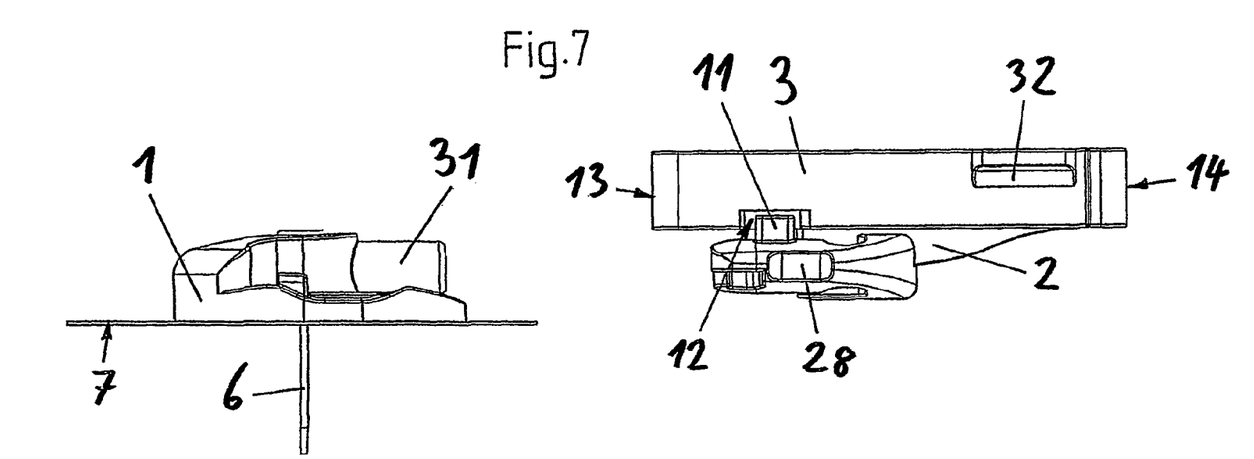
FIG. 7 is a side view of the arrangement of FIG. 1 after application, with the retraction device removed from the cannula housing.
Figure 8:
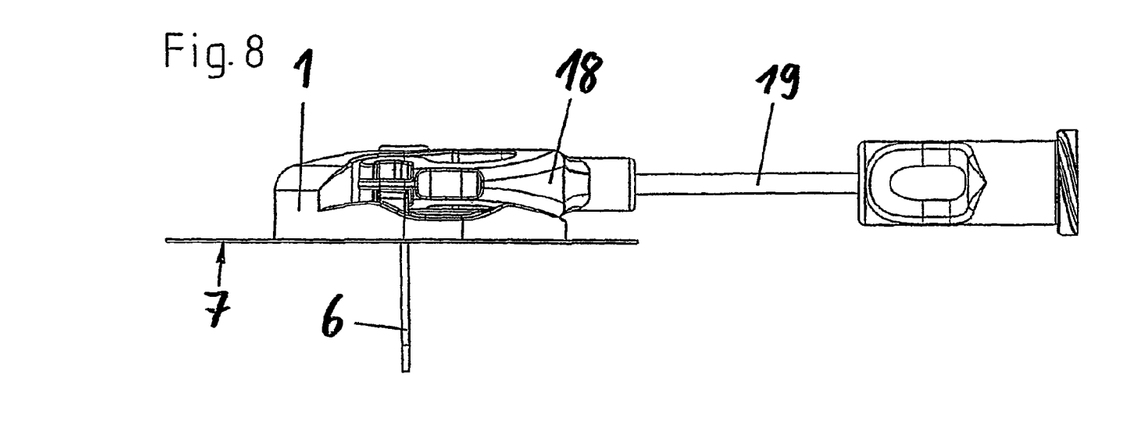
FIG. 8 is a side view of the applied cannula housing from FIG. 7 connected to a delivery tube.

The situation after separation of retraction device and cannula housing 1 is shown in a side view in FIG. 7. As will be seen, the removal of the retraction device means that the connection port 31 of the cannula housing 1 is accessible, such that a delivery tube 19 with a suitable connector piece 18 can be attached to the cannula housing 1 to deliver liquid medicaments through the channel 29 to the cannula 6. This situation is shown in FIG. 8.

Figure 9A:
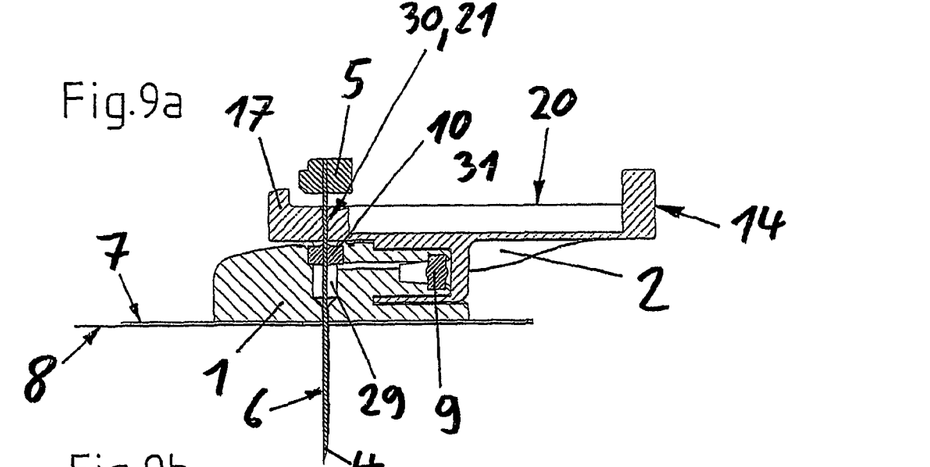
FIGS. 9a to 9c are longitudinal sections through the arrangement shown in FIG. 1 during production, in different stages of production.
Figures 9B, 9C:
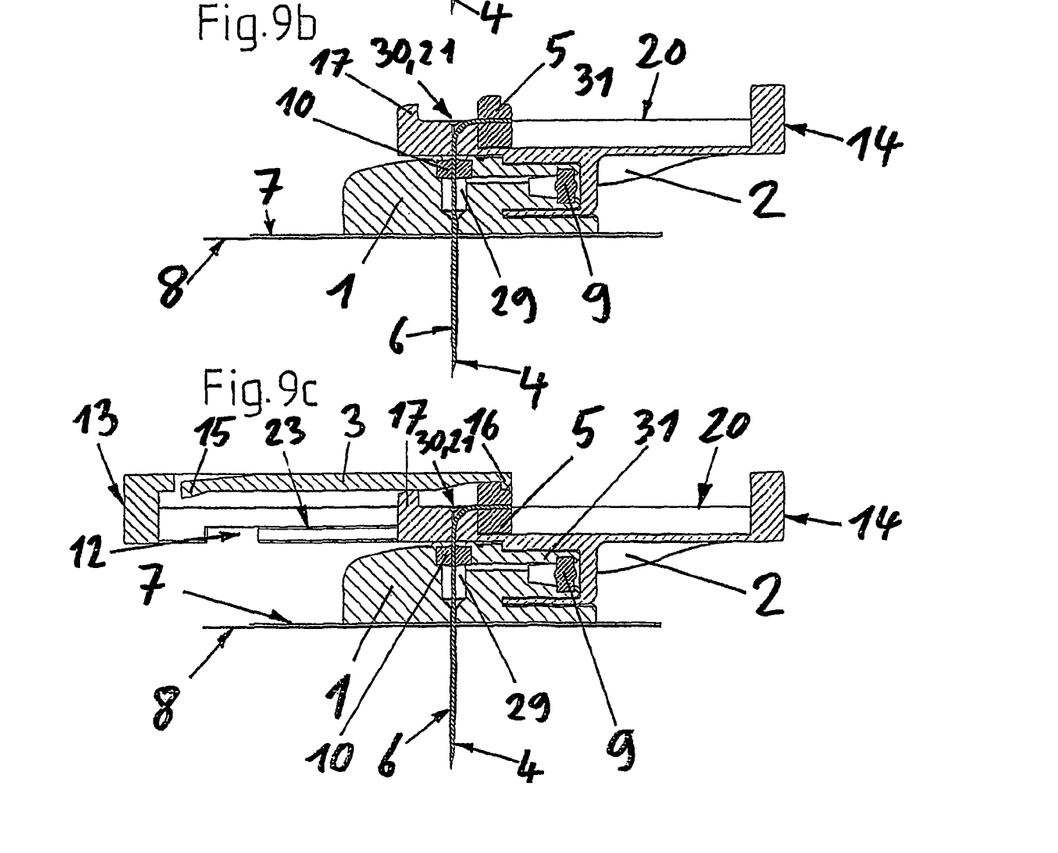

FIGS. 9a to 9c show longitudinal sections through the arrangement of FIG. 1 during its production, in various stages of production. As will be seen from FIG. 9a, after the fixed housing part 2 of the retraction device (which may be thought of as comprising elements 2, 3 and 5) has been secured on the cannula housing 1, the straight guide needle 4, connected at its end to the needle carrier 5, is introduced through the guide 21 of the deflection element 30 formed by the fixed housing part 2, and through the second septum 10 into the cannula channel of the flexible cannula 6, until the tip of the guide needle 4 protrudes from the outlet opening of the cannula 6. Then, with the aid of the needle carrier 5, the guide needle 4 is bent through 90° at the deflecting site of the deflection element 30, such that the needle carrier 5 comes to lie, as is intended, in a dedicated recess in the fixed housing part 2 of the retraction device. This situation is shown in FIG. 9b. The movable housing part 3 is then pushed with its guide rails 23 onto the guide rails 20 of the fixed housing part 2 until the locking projection 16 engages in a cutting provided for it on the needle carrier 5 and the movable housing part 3 can no longer be removed. This situation is shown in FIG. 9c and is identical to the original situation shown in FIGS. 1, 3 and 5.

Figure 12:
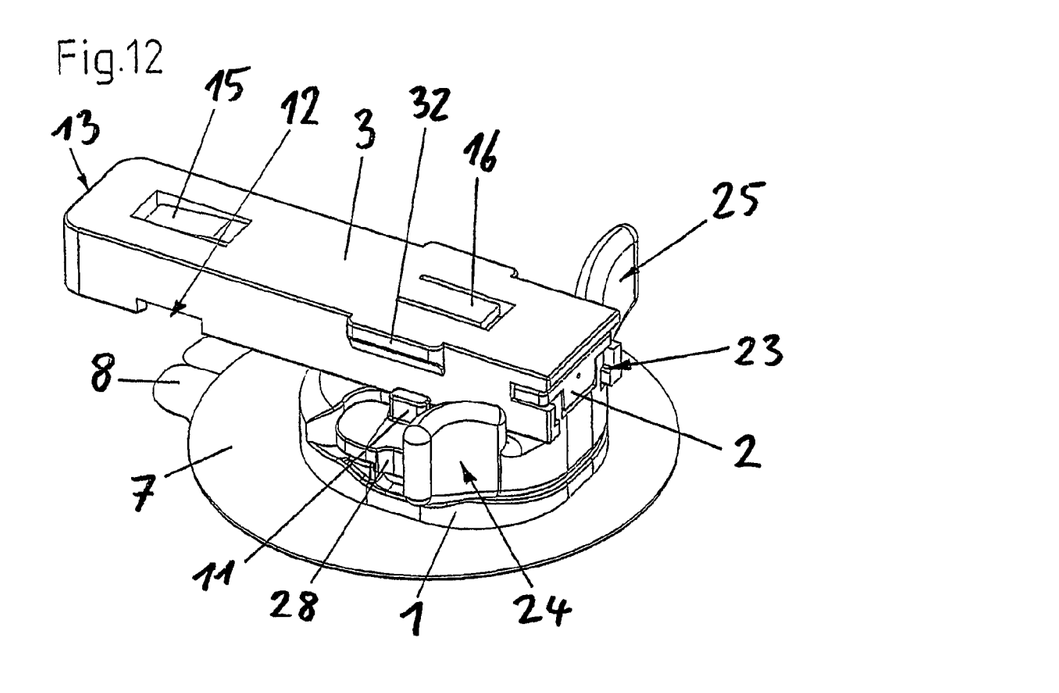
FIG. 12 is a perspective plan view of another embodiment of an arrangement according to the present invention before application.
Figure 13:
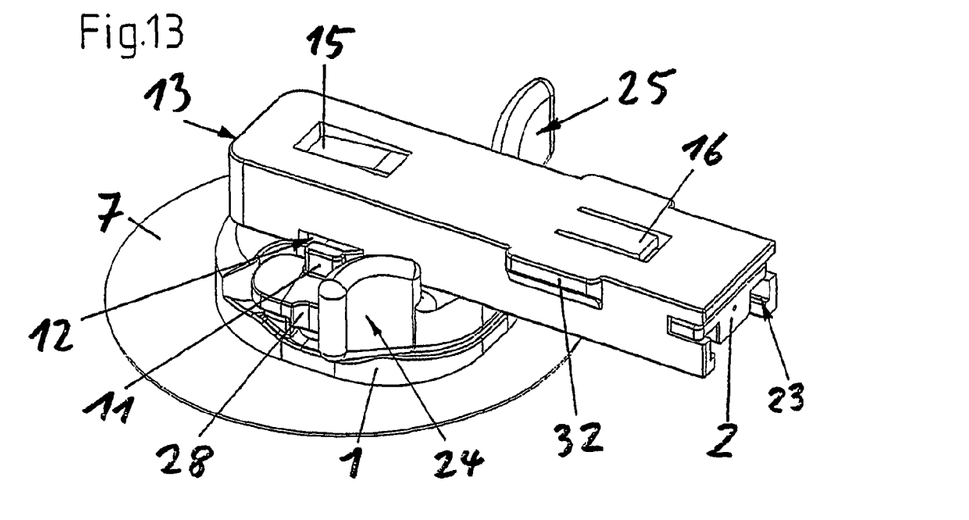
FIG. 13 is a perspective plan view of the arrangement of FIG. 12 after application.

FIGS. 12 and 13 show an alternative embodiment of the previously described infusion set, in the first instance in an unused original state (FIG. 12) and in the second instance in a state after application to the body of a patient (FIG. 13). In this embodiment, the retraction device (again comprising elements 2, 3 and 5) can be actuated with three fingers in a manner similar to the actuation of a syringe. For this purpose, the fixed housing part 2 has two grip surfaces 24, 25 for the pads of an index finger and middle finger, and the movable housing part 3 has an end face 13 onto which pressure can be applied using a thumb.

Figure 14:
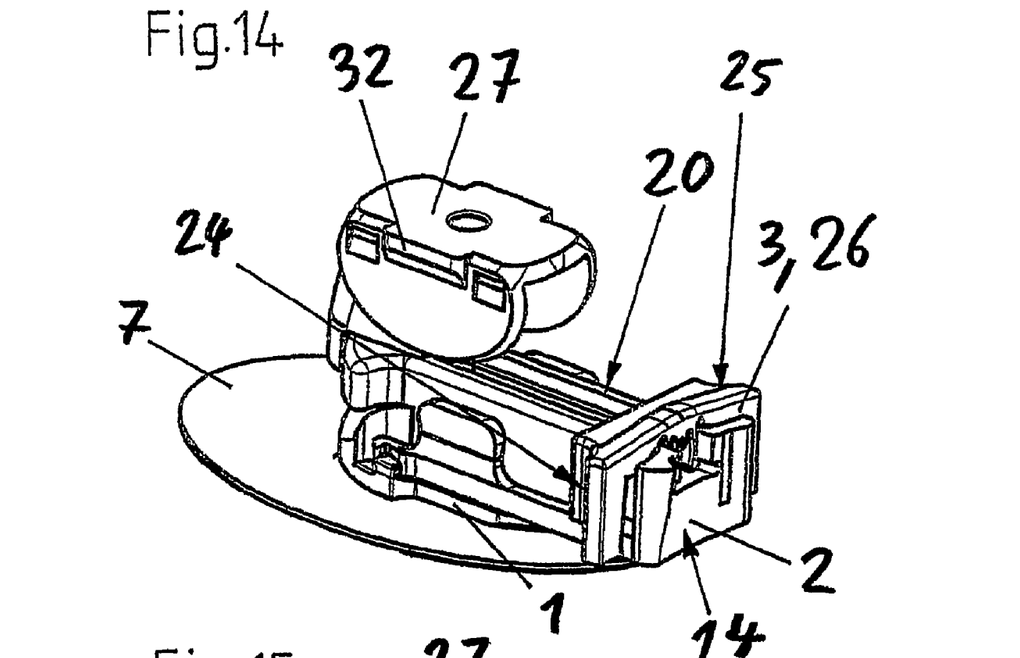
FIG. 14 is a perspective plan view of another embodiment of an arrangement according to the present invention after application.
Figure 15:
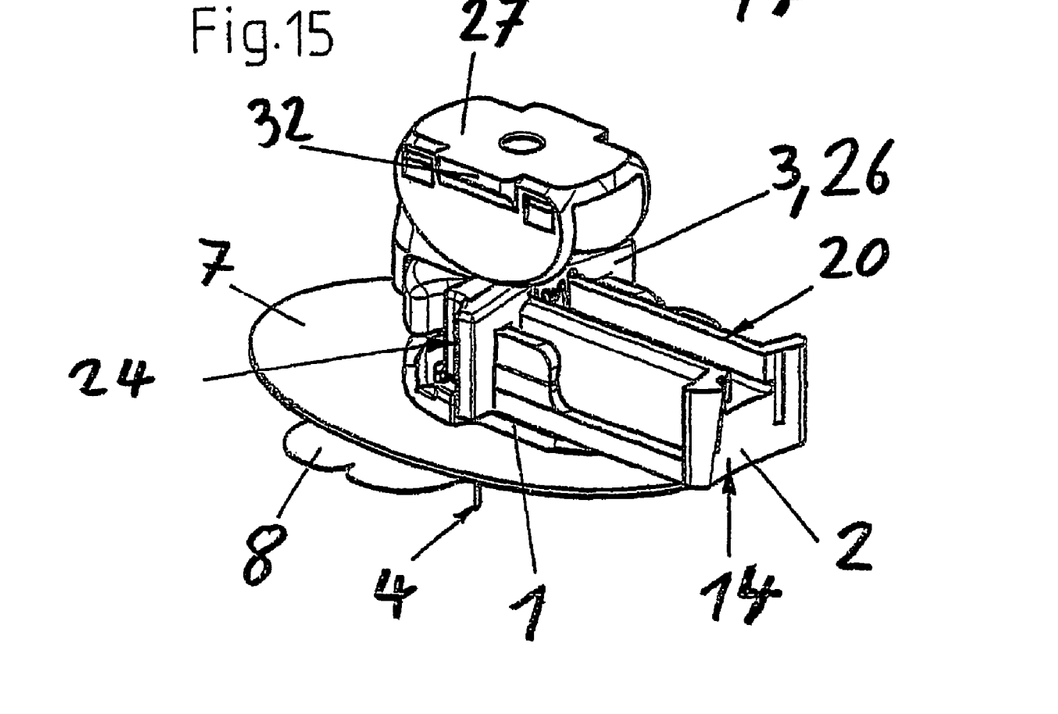
FIG. 15 is a perspective plan view of the arrangement of FIG. 14 before application.
Figure 16:
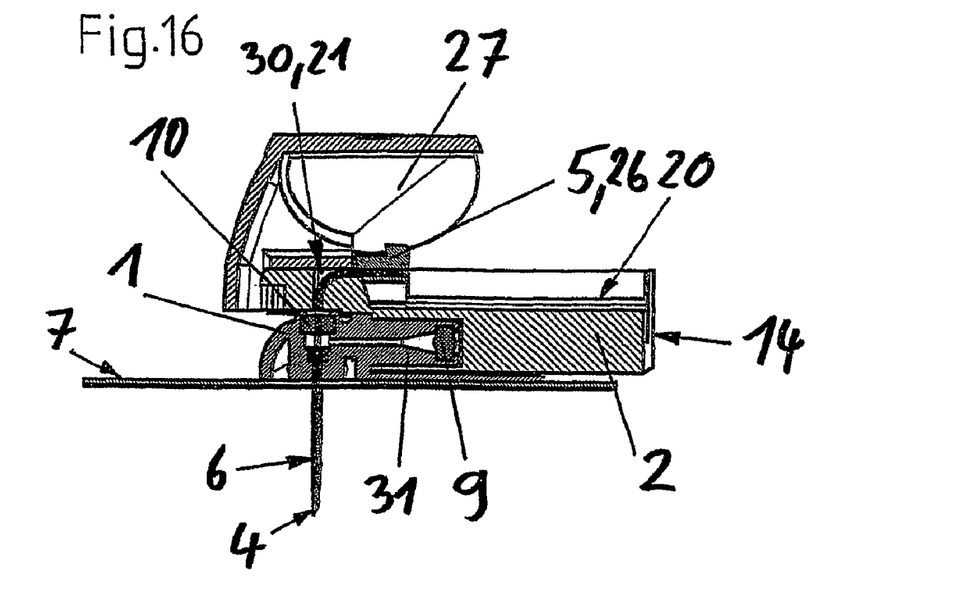
FIG. 16 is a longitudinal section through the arrangement shown in FIG. 15.
Figure 17:
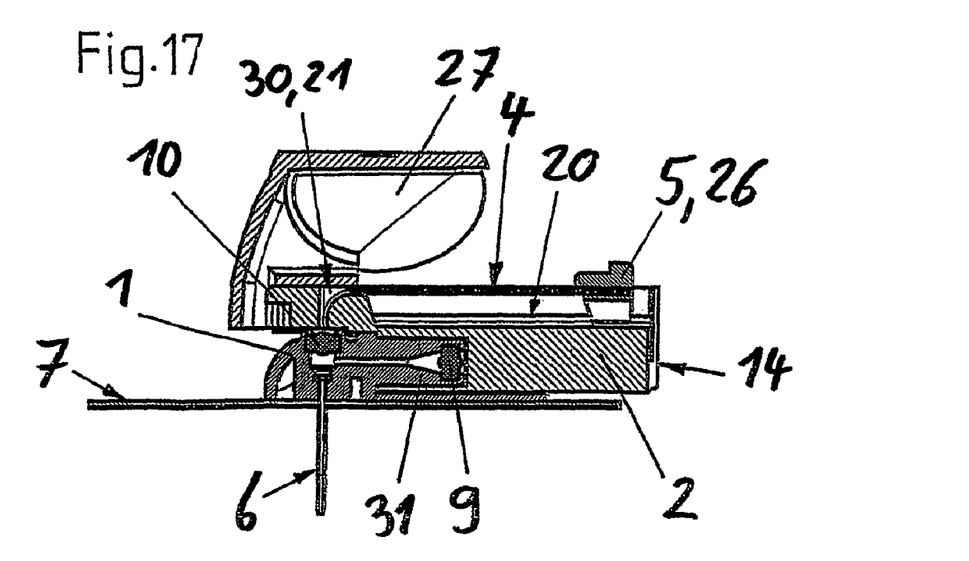
FIG. 17 is a longitudinal section through the arrangement shown in FIG. 14.

FIGS. 14 to 17 show, in perspective plan views and longitudinal sections, another embodiment of the arrangement according to the present invention in the form of an infusion set, in the first instance in an unused original state (FIGS. 15 and 16) and in the second instance in a state after application to the body of a patient (FIGS. 14 and 17). As will be seen from studying these figures, the infusion set has a structure similar to that described above, but with the difference that the movable housing part 3 and the fixed housing part 2 are not in this case pushed together to pull the guide needle 4 back. Instead, the movable housing part 3 is designed as a slide 26, which is displaceable in guides 20 along the fixed housing part 2 and which at the same time also forms the needle carrier 5 and, upon assembly, is snap-fitted into the guides 20. A further difference is that the fixed housing part 2 has a knob-like grip part 27, which is mounted thereon and can be taken hold of for application, or which can be secured on an application device by the securing shoulders 32 formed on it. Elements that are not explicitly described here, but that are provided with reference numbers, have the same function as the structural parts with corresponding reference numbers in the previously described embodiments.

Figure 18:
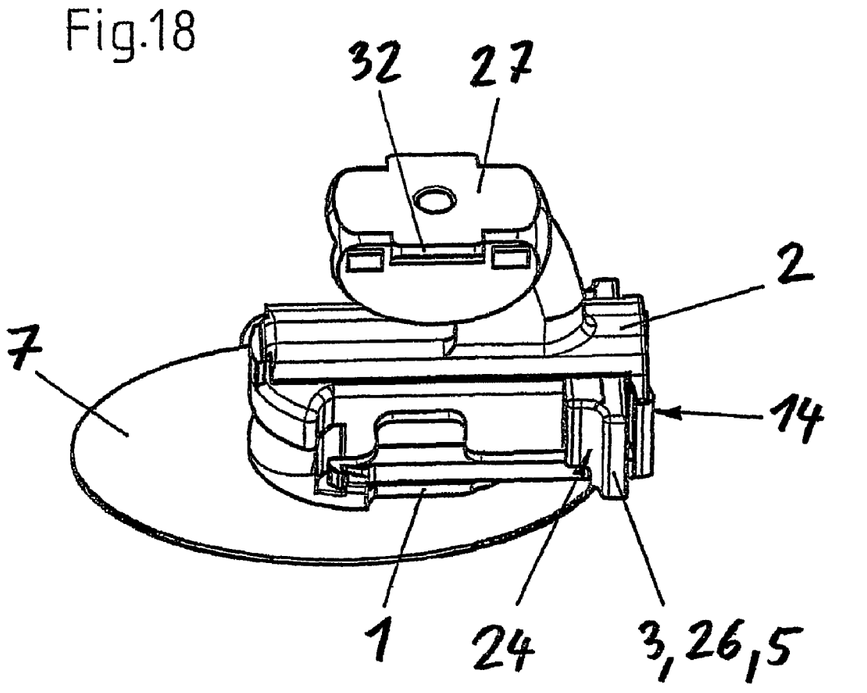
FIG. 18 is a perspective plan view of another embodiment of an arrangement according to the present invention after application.
Figure 19:
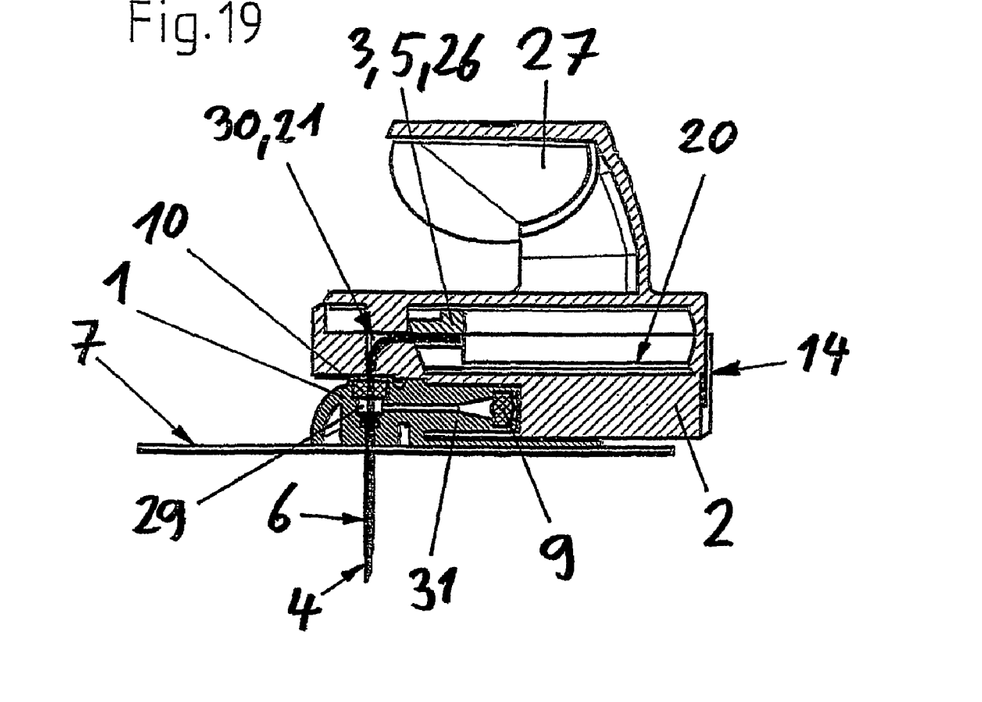
FIG. 19 is a longitudinal section through the arrangement of FIG. 18, but before application.
Figure 20:
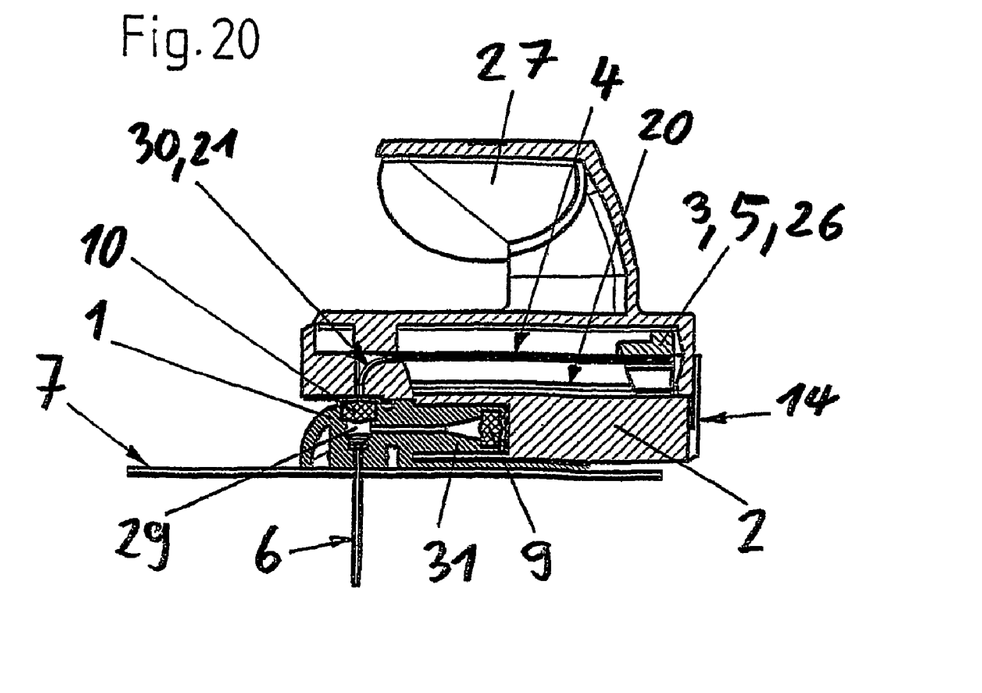
FIG. 20 is a longitudinal section through the arrangement shown in FIG. 18.

FIGS. 18 to 20 show, in a perspective plan view and in two longitudinal sections, another exemplary embodiment of the arrangement according to the present invention in the form of an infusion set, in the first instance in an unused original state (FIG. 19) and in the second instance in a state after application to the body of a patient (FIGS. 18 and 20). As will be seen from studying these figures, the infusion set has a structure similar to that shown in FIGS. 14 to 17. However, the difference is that the movable housing part 3, designed as slide 26, here protrudes laterally from the fixed housing part 2 only with two wings, which each present one of the grip surfaces 24, 25 for index finger and middle finger. A further difference is that the support structure of the knob-like grip part 27 is arranged at the other end of the fixed housing part 2 and, as will be seen from studying FIGS. 21a to 21d, is not mounted as a separate part onto the fixed housing part 2 but is instead formed in one piece with the latter. In this embodiment too, elements that are not explicitly described, but that are provided with reference numbers, have the same function as the structural parts with corresponding reference numbers in the previously described embodiments.

Figure 21A:
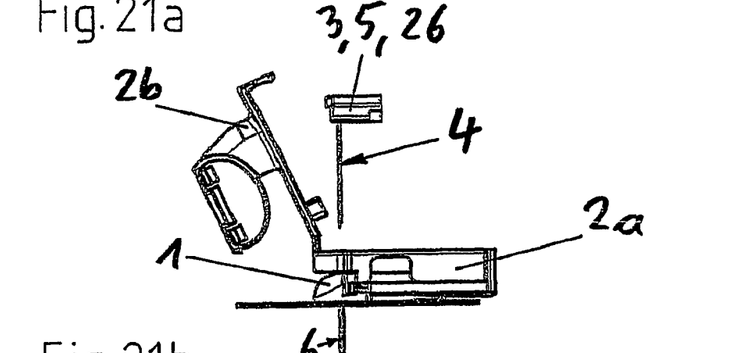
FIGS. 21a to 21d are schematic side views of the arrangement shown in FIG. 19 during production, in various stages of production.
Figure 21B:
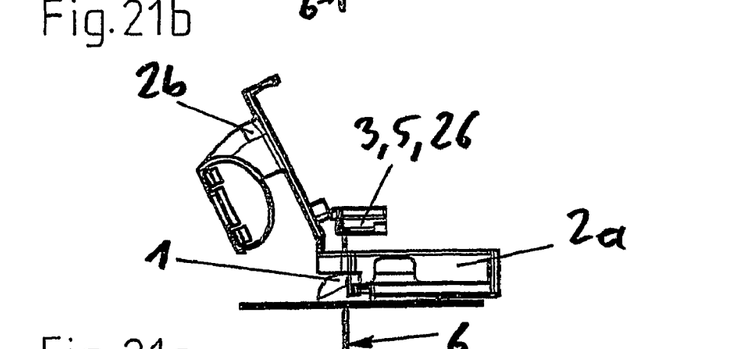
Figure 21C:
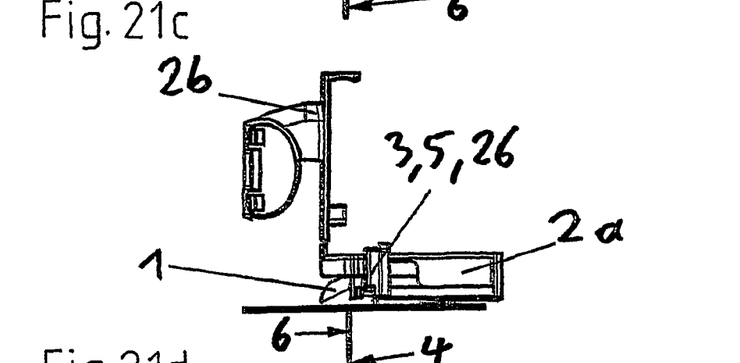
Figure 21D:
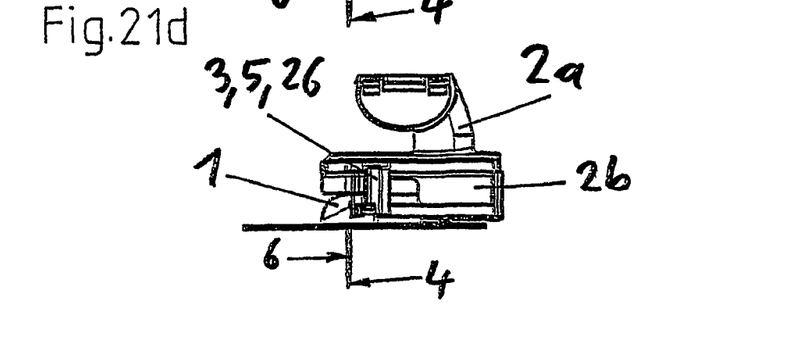

FIGS. 21a to 21d show schematic side views of the arrangement shown in FIGS. 18 to 20 during its production, in various stages of production. As will be seen, the infusion set here is produced using a fixed housing part 2 which is composed of two subelements 2a, 2b connected to each other via a hinge area and which is secured with the first subelement 2a on the cannula housing 1, while the second subelement is folded to the side (FIG. 21a). The straight guide needle 4, connected at its end to the movable housing part 3 designed as slide 26 and at the same time forming the needle carrier 5, is then introduced through the guide 21 of the deflection element 30 formed by the fixed housing part 2 and through the second septum 10 into the cannula channel of the flexible cannula 6, until the tip of the guide needle 4 emerges from the outlet opening of the cannula 6. With the aid of the movable housing part 3, the guide needle 4 is then bent through 90° round the deflecting site of the deflection element 30, such that the movable housing part 3 comes to lie, as is intended, in a dedicated recess in the first subelement 2a of the fixed housing part 2 of the retraction device (FIGS. 21b and 21c). The second subelement 2b of the fixed housing part 2 is then folded about the hinge area and locked irreversibly on the first subelement 2a, as a result of which the infusion set is made ready for application, as shown in FIG. 21d.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An infusion set for introducing a liquid into the body of a patient, the infusion set comprising:
    a cannula housing comprising a hollow cannula which protrudes from the housing;
    a guide needle inserted into the hollow cannula to guide the cannula into the body of the patient;
    a channel formed in the cannula housing, wherein the channel allows a medication to be guided to an inlet opening of the cannula;
    a sealing element positioned in an area opposite the inlet opening of the cannula, wherein the guide needle emerges from the cannula housing after the cannula is inserted into the body of the patient;
    a deflection element, wherein the guide needle is deflected in an axially displaceable manner, wherein the deflection element is arranged opposite where the guide needle emerges from the cannula housing, wherein the guide needle in an area between the cannula and its entry into the deflection element, has a rectilinear course;
    a retraction device for retracting the guide needle until it frees the inlet opening of the cannula, wherein the retraction device retracts the guide needle under the deflection by the deflection element.

2. The infusion set as claimed in claim 1, wherein the cannula housing, the deflection element and the retraction device are an inseparable unit.

3. The infusion set as claimed in claim 1, wherein the retraction device pulls the guide needle into a retraction end position, wherein the guide needle is completely out of the sealing element.

4. The infusion set as claimed in claim 3, wherein, in the retraction end position, the tip of the guide needle is arranged inside one of the deflection element or the retraction device.

5. The infusion set as claimed in claim 4, wherein when the guide needle is not in the retraction end position, the cannula housing, the deflection element and the retraction device form an inseparable unit.

6. The infusion set as claimed in claim 4, wherein when the guide needle is in the retraction end position, the retraction device and the deflection element are separable from the cannula housing.

7. The infusion set as claimed in claim 3, wherein the retraction device and the deflection element are inseparable unit and, in the retraction end position, the tip of the guide needle is inside the deflection element.

8. The infusion set as claimed in claim 1, wherein the retraction device comprises two structural parts which can be moved relative to each other.

9. The infusion set as claimed in claim 8, wherein one of the structural parts is fixed relative to the cannula housing and the second structural part is movable relative to the cannula housing and is coupled to the guide needle such that, upon movement of the two structural parts relative to each other, the guide needle is pulled by the second structural part.

10. The infusion set as claimed in claim 8, wherein the two structural parts can be pushed together in a translational movement.

11. The infusion set as claimed in claim 10, wherein the direction of pushing together the two structural parts is transverse to the direction of a longitudinal extent of the cannula such that the two structural parts extend substantially parallel to the surface of the skin.

12. The infusion set as claimed in claim 8, wherein one of the two structural parts has two grip surfaced spaced apart from each other in a direction transverse to the direction of pushing together of the structural parts and the other of the two structural parts has a grip surface opposite these two grip surfaces, such that the two structural parts can be pushed together.

13. The infusion set as claimed in claim 8, wherein the two structural parts are rotatable relative to each other.

14. The infusion set as claimed in claim 13, wherein the axis of rotation of the two structural parts extends parallel to the direction of the longitudinal extent of the cannula, such that the structural parts extend substantially perpendicular to the surface of the skin.

15. The infusion set as claimed in claim 8, wherein when the two structural parts are moved relative to each other, they lock together such that the guide needle is retracted.

16. The infusion set as claimed claim 1, wherein the guide needle is deflected through 90° in the deflection element.

17. An infusion set for introducing a substance into the body of a patient, the infusion set comprising:
  a cannula housing comprising a hollow cannula extending from the housing and a channel, wherein the channel provides a flowpath for a substance to flow to an inlet opening of the cannula;
  a guide needle for supporting the cannula as the cannula is inserted into the body of the patient, the guide needle being movable in the channel, wherein the guide needle is in the inlet opening after the cannula is inserted into the body of the patient;
  a deflection element for deflecting the guide needle during the movement of the guide needle in the channel, wherein the deflection is generally orthogonal; and
  a retraction device for retracting the guide needle from the inlet opening.

18. The infusion set according to claim 17, wherein the guide needle is deflected as it is being retracted.

* * * * *

UNITED STATES PATENT AND TRADEMARK OFFICE
CERTIFICATE OF CORRECTION

Page 1 of 1

PATENT NO. : 7,955,306 B2
APPLICATION NO. : 12/325459
DATED : June 7, 2011
INVENTOR(S) : Martin Wyss et al.

It is certified that error appears in the above-identified patent and that said Letters Patent is hereby corrected as shown below:

Col. 3, Line 30, "they from an" should read --they form an--

Col. 5, Line 45, "scope of the claims is definitely by" should read --scope of the claims is defined by--

Col. 11, Claim 12, Line 19, "grip surfaced spaced apart" should read --grip surfaces spaced apart--

Col. 12, Claim 16, Line 7, "claimed claim 1" should read --claimed in claim 1--

Signed and Sealed this
Fourth Day of October, 2011

David J. Kappos
*Director of the United States Patent and Trademark Office*